United States Patent [19]

Watanabe et al.

[11] 4,190,581
[45] Feb. 26, 1980

[54] NOVEL PENICILLIN DERIVATIVES

[75] Inventors: Yoshiaki Watanabe, Kodaira; Chihiro Yokoo, Gyoda; Toshifumi Asaka, Omiya; Jiro Sawada, Kodaira, all of Japan

[73] Assignee: Taisho Pharmaceutical Co., Ltd., Tokyo, Japan

[21] Appl. No.: 929,566

[22] Filed: Jul. 31, 1978

[30] Foreign Application Priority Data

Aug. 12, 1977 [JP] Japan .................................. 52-96726
Dec. 28, 1977 [JP] Japan .................................. 52-160559

[51] Int. Cl.² .................... C07D 499/50; C07D 401/04
[52] U.S. Cl. .................... 260/239.1; 424/250; 544/345
[58] Field of Search .................... 260/239.1; 544/345; 424/250

[56] References Cited

U.S. PATENT DOCUMENTS

| | | | |
|---|---|---|---|
| 3,951,955 | 4/1976 | Tobiki et al. | 260/239.1 |
| 3,954,733 | 5/1976 | Tobiki et al. | 260/239.1 |
| 4,005,075 | 1/1977 | Yamada et al. | 260/239.1 |
| 4,008,220 | 2/1977 | Tobiki et al. | 260/239.1 |
| 4,031,230 | 6/1977 | Gottschlich et al. | 260/239.1 |
| 4,092,309 | 5/1978 | Mich | 260/239.1 |
| 4,103,011 | 7/1978 | Minami et al. | 260/239.1 |

*Primary Examiner*—Norman Morgenstern
*Assistant Examiner*—Vera C. Clarke
*Attorney, Agent, or Firm*—Kenway & Jenney

[57] ABSTRACT

Novel penicillin derivatives of the formula

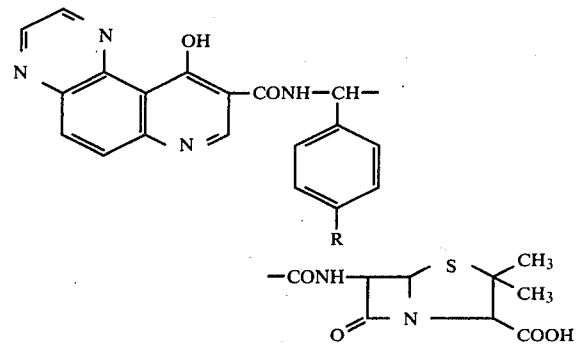

and pharmaceutically acceptable salts thereof, wherein R is hydrogen or hydroxy, are produced by acylating ampicillin, amoxicillin or a salt thereof with 4-hydroxy-pyrazino[2,3-f]quinoline-3-carboxylic acid or its functional derivative. They have high anti-pseudomonas activity and other antibacterial activity against gram-positive and gram-negative bacteria, and are of extremely low toxicity.

5 Claims, No Drawings

NOVEL PENICILLIN DERIVATIVES

BACKGROUND

Some naphthyridine and quinoline derivatives of ampicillin possessing antibacterial activity are disclosed in U.S. Pat. No. 3,951,955. They are, however, not of sufficiently low toxicity.

The present inventors have found that pyrazinoquinoline derivatives of penicillins of the formula (I) described hereinafter have excellent antipseudomonas activity and other antibacterial activity against gram-positive and gram-negative bacteria, and are of extremely lower toxicity as compared with the known penicillin derivatives.

DESCRIPTION AND PREFERRED EMBODIMENTS

The present invention relates to noval penicillin derivatives that are useful as pharmacological agents. More particularly, the present invention concerns with novel penicillin derivatives of the formula(I)

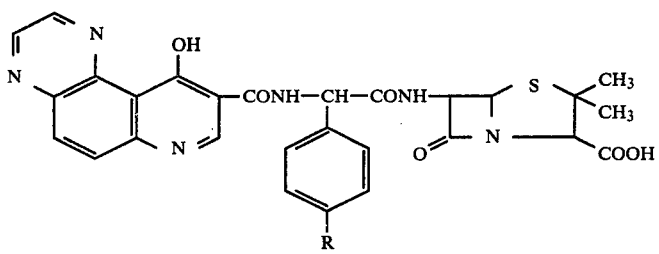

(I)

and pharmaceutically acceptable salts thereof, wherein R is hydrogen or hydroxy.

An object of the present invention is to provide some novel penicillin derivatives which are useful as antibacterial agents with extremely low toxicity, and are particular interest because of their activity against pseudomonas bacteria.

The compound of the formula(I) may be prepared by acylating ampicillin, amoxicillin or a salt thereof with a novel compound 4-hydroxy-pyrazino[2,3-f]quinoline-3-carboxylic acid or its functional derivative in an organic solvent. The acylation temperature is suitably in the range of 0° to 50° C.

Examples of the organic solvent are methylene chloride, chloroform, dioxane, acetonitrile, dimethylformamide, dimethyl sulfoxide, hexamethylphosphoric triamide and the like.

Examples of suitable functional derivative of 4-hydroxypyrazino [2,3-f]quinoline-3-carboxylic acid are the corresponding acid halides (e.g., chloride and bromide), acid azide, and active esters (e.g., N-hydroxysuccinimide and N-hydroxyphthalimide). These functional derivatives may be prepared by reacting 4-hydroxypyrazino [2,3-f]quinoline-3-carboxylic acid with a corresponding halogenating agent, azide forming agent or ester forming agent in a known manner per se.

When using 4-hydroxy-pyrazino[2,3-f]quinoline-3-carboxylic acid as the reactant, the reaction may be carried out in the presence of a condensing agent, e.g., carbodiimides such as dicyclohexylcarbodiimide, 1-ethoxycarbonyl-2-ethoxy-1,2-dihydroxyquinoline and isoxazolium salts such as Woodward's reagent.

Suitable salts of ampicillin or amoxicillin include the corresponding organic base salts, for example, trimethylamine, triethylamine or pyridine salt. They are well documented in the prior art.

4-Hydroxy-pyrazino[2,3-f]quinoline-3-carboxylic acid used as the reactant may be prepared by the following reaction sequence.

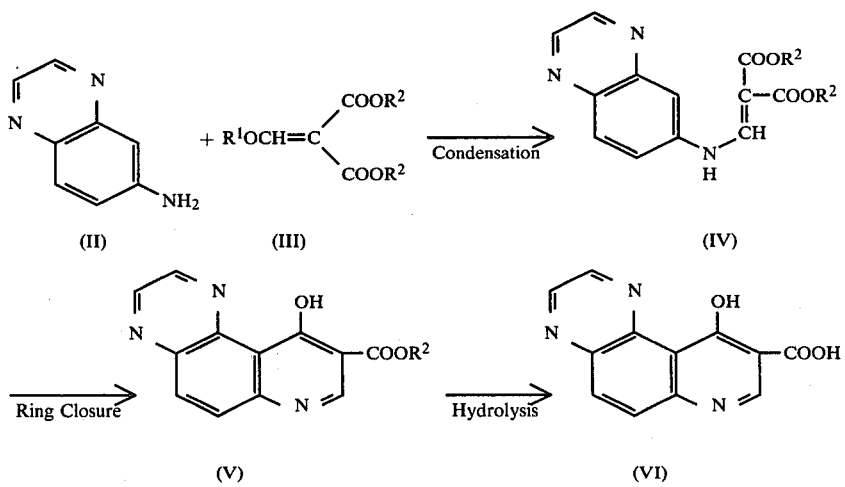

In this reaction sequence, $R^1$ and $R^2$ are the same or different alkyl containing 1 to 3 carbon atoms.

Condensation of 6-aminoquinoxaline(II) with a methylenemalonate (III) may be carried out with heating at 100° to 150° C. for 0.5 to 2 hours. Examples of methylenemalonate(III) are diethyl ethoxymethylenemalonate, dimethyl ethoxymethylenemalonate, diisopropyl methoxymethylenemalonate, and diethyl methoxymethylenemalonate.

Ring closure of N-(6-quinoxalyl)aminomethylenemalonate(IV) may be carried out in the presence of an organic solvent such as diphenyl, diphenyl ether or dibutyl phthalate, at the temperature of 250° to 300° C.

4-Hydroxy-pyrazino[2,3-f]quinoline-3-carboxylic acid(VI) may be obtained by hydrolysing a 4-hydroxy-pyrazino[2,3-f]quinoline-3-carboxylic acid ester(V) in the presence of a caustic alkali such as potassium hydroxide or sodium hydroxide at 25° C. to the boiling temperature, in a known manner per se.

The pharmaceutically acceptable salts of the compounds of the formula(I) include the corresponding alkali metal salts such as sodium and potassium salts, alkali earth metal salts such as calcium, barium and magnesium salts, unsubstituted and substituted ammonium salts, and arginine salt. They are obtained by reacting the compounds of the formula(I) with the corresponding base in a known manner per se.

The compounds of the present invention have high antipseudomonas activity and other antibacterial activity against gram-positive and gram-negative bacteria. For example, D-α-(4-hydroxy-pyrazino[2,3-f]quinoline-3-carbonamido)benzylpenicillin sodium salt(TPC-20) and D-α-(4-hydroxy-pyrazino[2,3-f]quinoline-3-carbonamido)-p-hydroxybenzylbenzylpenicillin sodium salt(TAC-20) give the minimal inhibitory concentrations as shown in Table 1, by the agar dilution method.

TABLE 1

|  | TPC-20 | TAC-20 | AMPICILLIN | CARBENICILLIN |
|---|---|---|---|---|
| S. aureus 209 P | 0.1 | 1.6 | <0.05 | 0.4 |
| S. smith | 0.4 | 0.8 | <0.05 | 0.4 |
| E. coli NIHJ 2 | 1.56 | 3.1 | 6.2 | 6.2 |
| E. coli B | <0.05 | 0.4 | 0.2 | 0.8 |
| Kleb. pneumo. | 0.8 | 1.6 | 12.5 | 50 |
| Kleb. pneumo. 309 | 3.1. | 12.5 | 50 | >400 |
| Ent. cloacae IFO 13535 | 3.1 | 6.2 | ≧200 | 25 |
| Proteus vulgaris | 0.8 | 1.6 | 0.8 | 0.8 |
| Serratia marc. IID 618 | 0.4 | 3.1 | 12.5 | 3.1 |
| Sal. enteritidis | 0.8 | 0.8 | 0.2 | 0.8 |
| Ps. aeruginosa NC 5 | 12.5 | 12.5 | ≧200 | 100 |
| Ps. aeruginosa GNB 1-1-1 | 3.1 | 3.1 | >400 | 50 |
| Ps. aeruginosa IID 1052 | 3.1 | 6.2 | ≧200 | 25 |

(Numbers:μg/ml)

The compounds of the present invention may be used as antibacterial agents in the same manner as other penicillins. For example, they may be used in mammals in an amount of about 1 mg to 100 mg/kg, daily, parenterally, in single or two to four divided doses to treat infections of bacterial origin, e.g., 10 mg/kg in mice.

The compounds of the present invention are of low toxicity. That is, they hardly show any intraperitoneal acute toxicity in rats at a dose less than 5000 mg/kg of body weight.

The compounds of the present invention may be used alone or in combination as the active ingredients in any one or a variety of pharmaceutical preparations. They may be administered by parenteral injections such as subcutaneous, intramuscular or intravenous injection, in the form of solution or suspension in suitable media, e.g., sterile water, saline, glycols, oils, or as dry preparations suitable for the extempore preparation of injectable forms. In addition, the compounds of the present invention may be administered in the form of suppository in suitable media, e.g., stearic acid, its salt, talc, vegitable oils and glycols.

The present invention is further illustrated by the following detailed examples which are not intended to limit the scope of the present invention.

EXAMPLE 1

D-α-(4-hydroxy-pyrazino[2,3-f]quinoline-3-carbonamido)-benzylpenicillin sodium salt Step A diethyl N-(6-quinoxalyl)aminomethylenemalonate A mixture of 6-aminoquinoxaline(19.2 g) and diethyl ethoxymethylenemalonate(34.8 g) was heated for an hour at 110° C. After filtration, the crystals thus obtained were crystallized from ethanol to give diethyl N-(6-quinoxalyl)aminomethylenemalonate (37.5 g) as pale yellow needles, m.p. 112°–114° C.

Step B ethyl 4-hydroxy-pyrazino[2,3-f]quinoline-3-carboxylate

Diethyl N-(6-quinoxalyl)aminomethylenemalonate(37.5 g) was gradually added to diphenyl ether(300 ml) at 260°–280° C. The resulting mixture was heated for an additional hour at the same temperature. After cooling, the mixture was mixed with n-hexane (500 ml), and filtered off. The resulting solid was washed with n-hexane and acetone to give ethyl 4-hydroxy-pyrazino[2,3-f]quinoline-3-carboxylate(28.8 g) as a colorless powder, m.p. 223°–225° C.

Step C 4-hydroxy-pyrazino[2,3-f]quinoline-3-carboxylic acid

A mixture of ethyl 4-hydroxy-pyrazino[2,3-f]quinoline-3-carboxylate(28.8 g) and 10% potassium hydroxide solution(350 ml) was heated under reflux for an hour. The resulting reaction solution was acidified with a concentrated hydrochloric acid. After filtration, the resulting solid was washed with water and acetone, and then dried over phosphorus pentoxide to give 4-hydroxy-pyrazino[2,3-f]quinoline-3-carboxylic acid(23.5 g) as pale yellow crystalline powders, m.p. >300° C.

Anal. Calcd. for $C_{11}H_7N_3O_3$: C, 59.75; H, 2.93; N, 17.42. Found: C, 59.40; H, 3.17; N, 17.23.

Step D

N-hydroxysuccinimide ester of 4-hydroxy-pyrazino[2,3-f]quinoline-3-carboxylic acid 4-Hydroxy-pyrazino[2,3-f]quinoline-3-carboxylic acid(2.41 g) was refluxed with thionyl chloride(15 ml)

for an hour, and then concentrated in vacuo. To the residue were added N-hydroxysuccinimide(1.27 g), N,N-dimethylformamide(50 ml) and pyridine (2 ml). The resultant mixture was stirred for 2 hours at room temperature. The solid product was collected, washed with N,N-dimethylformamide and acetone, and then dried over phosphorus pentoxide to give N-hydroxysuccinimide ester of 4-hydroxy-pyrazine[2,3-f]quinoline-3-carboxylic acid(2.34 g), m.p. 261°–263° C.(decomp.).

Step E

D-α-(4-hydroxy-pyrazino[2,3-f]quinoline-3-carbonamide)benzylpenicillin sodium salt A solution of ampicillin trihydrate(403 mg), triethylamine (0.42 ml) and methylene chloride(10 ml) was dried over anhydrous magnesium sulfate. The dried solution was added to a stirred suspension of N-hydroxysuccinimide ester of 4-hydroxy-pyrazino[2,3-f] quinoline-3-carboxylic acid(338 mg) in hexamethylphosphoric triamide (10 ml) at room temperature. The resulting mixture was gently stirred for 6 hours at the same temperature. After addition of methylene chloride(50 ml), the reaction mixture was acidified to pH 2 with 10% hydrochloric acid. The organic layer was separated and dried over anhydrous magnesium sulfate. After removal of the solvent in vacuo, the residue was dissolved in ethyl acetate(50 ml) and added to a 30% n-butanol solution of sodium 2-ethylhexanoate. After filtration, the separated crystals were washed with ethyl acetate and ether, and then died over phosphorus pentoxide to give D-α-(4-hydroxy-pyrazino[2,3-f]quinoline-3-carbonamido)benzylpenicillin sodium salt(494 mg), m.p. 235° C. (decomp.)

IR: $\nu_{max}^{KBr}$ 1765 cm$^{-1}$ (β-lactam C=O)

NMR: (DMSO-d$_6$), δ1.48 (3H, s), 1.60 (3H, s), 4.05 (1H, s), 5.30–5.70 (2H, m), 6.02 (1H, d, J=8 Hz), 7.10–7.70 (5H, m), 8.14 (2H, s), 8.82 (1H, s), 8.89 (1H, d, J=2 Hz), 8.90–9.30 (1H, broad), 9.07 (1H, d, J=2 Hz), 11.31 (1H, d, J=8 Hz).

EXAMPLE 2

D-α-(4-hydroxy-pyrazino[2,3-f]quinoline-3-carbonamido)-p-hydroxybenzylpenicillin sodium salt A solution of amoxicillin trihydrate(419 mg), triethylamine (0.42 ml), methylene chloride(7 ml) and hexamethylphosphoric triamide (7 ml) was dried over anhydrous magnesium sulfate. The dried solution was added dropwise to a suspension of N-hydroxysuccinimide ester of 4-hydroxy-pyrazino[2,3-f]quinoline-3-carboxylic acid(338 mg) in hexamethylphosphoric triamide. The reaction mixture was treated by a manner similar to that described in Example 1, Step E to give D-α-(4-hydroxy-pyrazino[2,3-f]quinoline-3-carbonamido)-p-hydroxy-benzylpenicillin sodium salt (385 mg), m.p. 223°–226° C. (decomp.).

IR: $\nu_{max}^{KBr}$ 1763 cm$^{-1}$ (β-lactam C=O)

NMR: (DMSO-d$_6$), δ1.49 (3H, s), 1.61 (3H, s), 4.05 (1H, s), 5.34–5.52 (2H, m), 5.86 (1H, d, J=7 Hz), 6.72 (2H, d, J=8 Hz), 7.33 (2H, d, J=8 Hz), 8.16 (2 H, s), 8.82 (1H, s), 8.85–9.15 (1H, broad), 8.92 (1H, d, J=2 Hz), 9.10 (1H, d, J=2 Hz), 11.12 (1H, d, J=7 Hz).

What is claimed is:

1. Penicillin derivatives of the formula

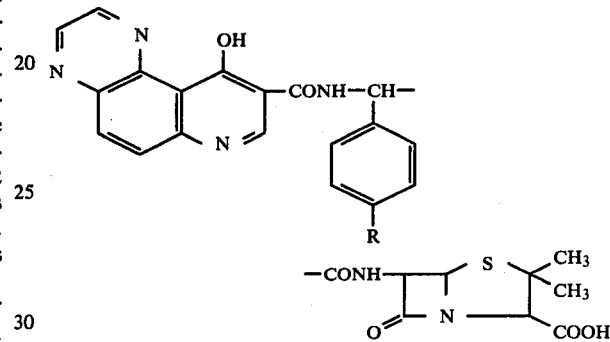

and pharmaceutically acceptable salts thereof, wherein R is hydrogen or hydroxy.

2. A compound according to claim 1 which is D-α-(4-hydroxypyrazino[2,3-f]quinoline-3-carbonamido)benzylpenicillin and pharmaceutically acceptable salts thereof.

3. A compound according to claim 1 which is D-α-(4-hydroxypyrazino[2,3-f]quinoline-3-carbonamido)-p-hydroxybenzyl penicillin and pharmaceutically acceptable salts thereof.

4. A compound selected from the group consisting of 4-hydroxy-pyrazino[2,3-f]quinoline-3-carboxylic acid, its acid azide, its acid halides, and its esters with N-hydroxysuccinimide and N-hydroxyphthalimide.

5. A compound according to claim 4 which is N-hydroxysuccinimide ester of 4-hydroxy-pyrazino[2,3-f]quinoline-3-carboxylic acid.

* * * * *